(12) United States Patent
Wolfe

(10) Patent No.: US 6,954,701 B2
(45) Date of Patent: *Oct. 11, 2005

(54) METHOD FOR REMOTE MONITORING OF WATER TREATMENT SYSTEMS

(75) Inventor: Thomas D. Wolfe, Rough and Ready, CA (US)

(73) Assignee: Watereye, Inc., Grass Valley, CA (US)

(*) Notice: Subject to any disclaimer, the term of this patent is extended or adjusted under 35 U.S.C. 154(b) by 68 days.

This patent is subject to a terminal disclaimer.

(21) Appl. No.: 10/695,627

(22) Filed: Oct. 27, 2003

(65) Prior Publication Data

US 2004/0138840 A1 Jul. 15, 2004

Related U.S. Application Data

(63) Continuation-in-part of application No. 10/392,112, filed on Mar. 19, 2003, which is a continuation-in-part of application No. 10/055,225, filed on Oct. 26, 2001, now Pat. No. 6,560,543, which is a continuation-in-part of application No. 09/213,781, filed on Dec. 17, 1998, now Pat. No. 6,332,110.

(51) Int. Cl.[7] ............................................... B01D 15/00
(52) U.S. Cl. ........................ 702/22; 702/30; 702/31; 702/188; 210/141; 210/634; 210/638; 210/660; 700/270; 700/271
(58) Field of Search .................. 702/22, 30, 31, 702/188; 210/634, 638, 660, 141; 700/270, 271

(56) References Cited

U.S. PATENT DOCUMENTS

| | | | |
|---|---|---|---|
| 4,830,757 A | 5/1989 | Lynch et al. | |
| 5,492,632 A | 2/1996 | Reber | |
| 5,608,171 A | 3/1997 | Hunter et al. | |
| 5,631,744 A | 5/1997 | Takeuchi et al. | |
| 5,832,410 A | 11/1998 | Lin et al. | |
| 5,835,724 A | 11/1998 | Smith | |
| 5,865,718 A | 2/1999 | Chan | |
| 5,970,426 A | 10/1999 | Mandel et al. | |
| 5,993,662 A | 11/1999 | Garr et al. | |
| 6,023,223 A | 2/2000 | Baxter, Jr. | |
| 6,061,603 A | 5/2000 | Papadopoulos et al. | |
| 6,305,944 B1 | 10/2001 | Henry et al. | |
| 6,317,639 B1 | 11/2001 | Hansen | |
| 6,332,110 B1 * | 12/2001 | Wolfe | 702/22 |
| 6,356,205 B1 | 3/2002 | Salvo et al. | |
| 6,370,448 B1 | 4/2002 | Eryurek | |
| 6,389,331 B1 | 5/2002 | Jensen et al. | |
| 6,560,543 B2 * | 5/2003 | Wolfe et al. | 702/22 |
| 2001/0020195 A1 | 9/2001 | Patel et al. | |
| 2001/0053992 A1 | 12/2001 | Eto et al. | |
| 2002/0023479 A1 | 2/2002 | Burge et al. | |
| 2002/0130069 A1 | 9/2002 | Moskoff | |
| 2002/0133270 A1 | 9/2002 | Hung et al. | |

FOREIGN PATENT DOCUMENTS

WO   WO 01/80494   10/2001

* cited by examiner

Primary Examiner—Bryan Bui
Assistant Examiner—Hien Vo
(74) Attorney, Agent, or Firm—McHale & Slavin, P.A.

(57) ABSTRACT

A method of monitoring the daily operating performance parameters for water treatment processes through the collection of localized data. The data is manipulated to generate preconfigured performance, maintenance, and quality assurance reports and further provide automatic submission of data as required for regulatory review of certain water treatment systems such as potable water treatment. The data is collected from sensors located at an equipment site and transferred to a remote computer located by use of the Internet, further all data received and used for generation of reports is also accessible by Internet connection and be delivered directly to the regulatory agency without additional process.

23 Claims, 3 Drawing Sheets

METHOD FOR REMOTE MONITORING OF WATER TREATMENT SYSTEMS

CROSS REFERENCE TO RELATED APPLICATIONS

This Application is a continuation-in-part application of application Ser. No. 10/392,112, filed Mar. 19, 2003, which is a continuation-in-part of application Ser. No. 10/055,225 filed Oct. 26, 2001 now U.S. Pat. No. 6,560,543, which is a continuation-in-part of application Ser. No. 09/213,781 filed Dec. 17, 1998 now U S. Pat. No. 6,332,110, the contents of which are incorporated herein by reference.

FIELD OF THE INVENTION

This invention is related to the field of water treatment, and in particular, to a method of monitoring advanced separation and/or ion exchange processes by use of the world wide web allowing review of data collected and compiled asynchronously from a web server.

BACKGROUND OF THE INVENTION

Potable water is essential, with quality and safety standards regulated by the Environmental Protection Agency (EPA) in accordance with the Public Water System Supervision program. The standards are enforced by local agencies. There are over 170,000 water districts in the United States which provide public drinking water to 90% of Americans.

The EPA has primary standards designed to protect public health against substances that may be harmful to humans if consumed. EPA secondary standards ensure the aesthetic qualities of water such as taste, odor, or clarity. However, each water district remains responsible for monitoring the drinking water itself to ensure that it meets all drinking water standards. The treatment processes for the drinking water must be monitored as well.

In order to comply with the regulatory testing calendar, water districts are required to report a battery of analytical test results varying from quarterly to yearly, depending on the source of the water supply. Water systems must monitor their drinking water to ensure that it is safe for their customers. Monitoring schedules differ according to the type of contaminants that may be present in a given water supply. The quarterly tests are typically chlorine and turbidity, which can be accomplished with automatic analyzers. Water districts use electronic sensors to monitor the amount of storage, discharge pressure and flow from the systems on a daily basis. Other parameters which are not automatically sensed, but rather are determined by analytical tests, are reported to regulatory agencies on a periodic basis.

Municipal water may be obtained from any source, including seawater, all of which can be made potable by use of proper water treatment equipment. For instance, a reverse osmosis system is capable of lowering the total dissolved solids of sea water to drinking water levels. Despite the sophistication of pretreatment, improper operation can lead to fouled membranes. If fouling occurs but is found quickly, the membranes may be cleaned averting water contamination and associated water treatment repairs. However, if the fouling is not detected quickly, the water treatment system can be irreparably damaged and lead to human health concerns.

One of the problems with maintaining advanced processing equipment is a need for highly qualified individuals. Employment of a full time staff is costly and can be problematic since such monitoring is repetitive and highly qualified individuals can easily become bored. For this reason, all water treatment processes include a large assortment of strategically placed sensors that are typically incorporated into a computer system capable of comparing the sensor values against a pre-set quality level. However, if the operator does not recognize a particular alarm condition, the elaborate array of monitoring equipment is useless.

Municipal water treatment plants are ultimately the responsibility of elected officials. Yet these officials rarely have the technical training or time to allow them to directly access the performance parameters of the systems for which they are responsible. The present invention could easily be used to provide a readily understandable presentation of the current performance of a municipal water treatment system which was fully accessible by the elected officials as well as plant operators, at any time via the Internet, but which provided no access to the control system of the water treatment plant. In addition, in this application of the technology, the same presentation of the system performance could be made accessible to the public at large, allowing interested members of the public to monitor the operation of their own drinking water plants as desired.

Thus, what is lacking in the art, is a means for monitoring water treatment processes in a cost effective manner by highly trained personnel providing regulatory reporting with a real time analysis that can be simultaneously viewed and verified at any time by multiple parties, from any location having access to the Internet, but which provided no access to the control system of the water treatment plant.

SUMMARY OF THE INVENTION

The instant invention is a method of monitoring water treatment systems, particularly those subject to regulatory reporting such as potable water treatment systems. The method includes the collection of data which are manipulated to generate preconfigured performance, maintenance, quality assurance, quality control, regulatory performance graphing, historical trends, and regulatory reports. The raw data is collected from sensor assemblies located at an equipment site which are networked to a server computer. The raw data may be transferred to the server computer in real time. The data received at the server computer can be used for the generation of reports also accessible by Internet connection. The reports, graphs and information can be viewed online or downloaded by use of a web browser. Regulatory reports can be forwarded automatically to the regulatory agency via electronic transmission means with the added benefit of receiving reports generated directly from the sensor input thereby eliminated the possibility of human error or tampering. The method allows a single location to monitor countless customers with each customer capable of reviewing information relevant to their equipment, all information is kept confidential by use of appropriate account names, protocols and passwords.

Thus, a primary objective of the instant invention is to provide a method of monitoring water treatment systems by compiling information from one or more sensor assemblies which are in direct communication with a server computer to generate operational information in near real time, if desired, which can be obtained from any location having access to the Internet. The compiled information can be placed into the required format required by regulatory agencies.

Another objective of the instant invention is to provide a system that operates independent of the water treatment system wherein no feedback is possible to any monitoring or control system and to transfer such information by a local Internet provider or other internet connection to a consolidating Internet address.

Yet another objective of the instant invention is to provide an Internet report system that can be viewed online or offline providing alarms by the use of current and historical records.

Still another objective of the instant invention is to provide automatic real-time transmission of sensor data, data to graph conversion, data to statistical report conversation, compliance calendars, e-mail notification of compliance and the ability to automatically file data and reports with the regulatory agency.

Yet another objective of the instant invention is to provide scheduled and predicted maintenance reports by the use of the current and historical records; providing emergency notification of failures, shutdowns, critical parameters, membrane damage and the like by the use of electronic mail, pager, and/or human voice calling.

Another objective of the instant invention is to enable regulatory reporting without the need for human interface thereby negating human error or tampering.

Still another objective of the instant invention is to provide a method of regulatory reporting which is independent and/or complimentary of the existing monitoring system.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

The instant invention is a monitoring system that incorporates the use of the Internet for providing a remote location for assimilation and dissemination of configured reports regarding water treatment systems primarily for the purpose of preparing and submitting regulatory reports required for operation of certain water treatment systems. Data is first collected on site at a water treatment facility by the use of at least one sensor assembly. Each sensor assembly includes a sensor and a communications interface, which interface may be formed integral therewith. One or more sensor assemblies and on-line analytical devices are utilized for transmitting raw data collected from numerous locations on a water treatment system.

In a preferred embodiment, the sensors are micro-sensors that incorporate chemically selective sensors and physical measurement devices on a single chip of silicon or other functional material that can chemically profile a sample as small as a drop. In a preferred embodiment the sensors include a communications interface effective for real time data transmission, such as a Lonworks® network variable interface. Suitable sensors would include the Six-CENSE™ and CT-CENSE™ manufactured by Dascore, Inc., as well as the multi-sensor devices manufactured by Sensicore, Inc. These sensors can measure chlorine, heavy metals, and various other constituents by concentrating the analyte through a small membrane exposed to the stream being monitored. Electric current (amperometric) or voltage readings are then converted to a value by the control electronics within the device. Critical water parameters to be measured include, but are not limited to, free chlorine and monochloramine, dissolved oxygen, pH, conductivity, oxidation-reduction potential, temperature, color and turbidity.

Figure 1:
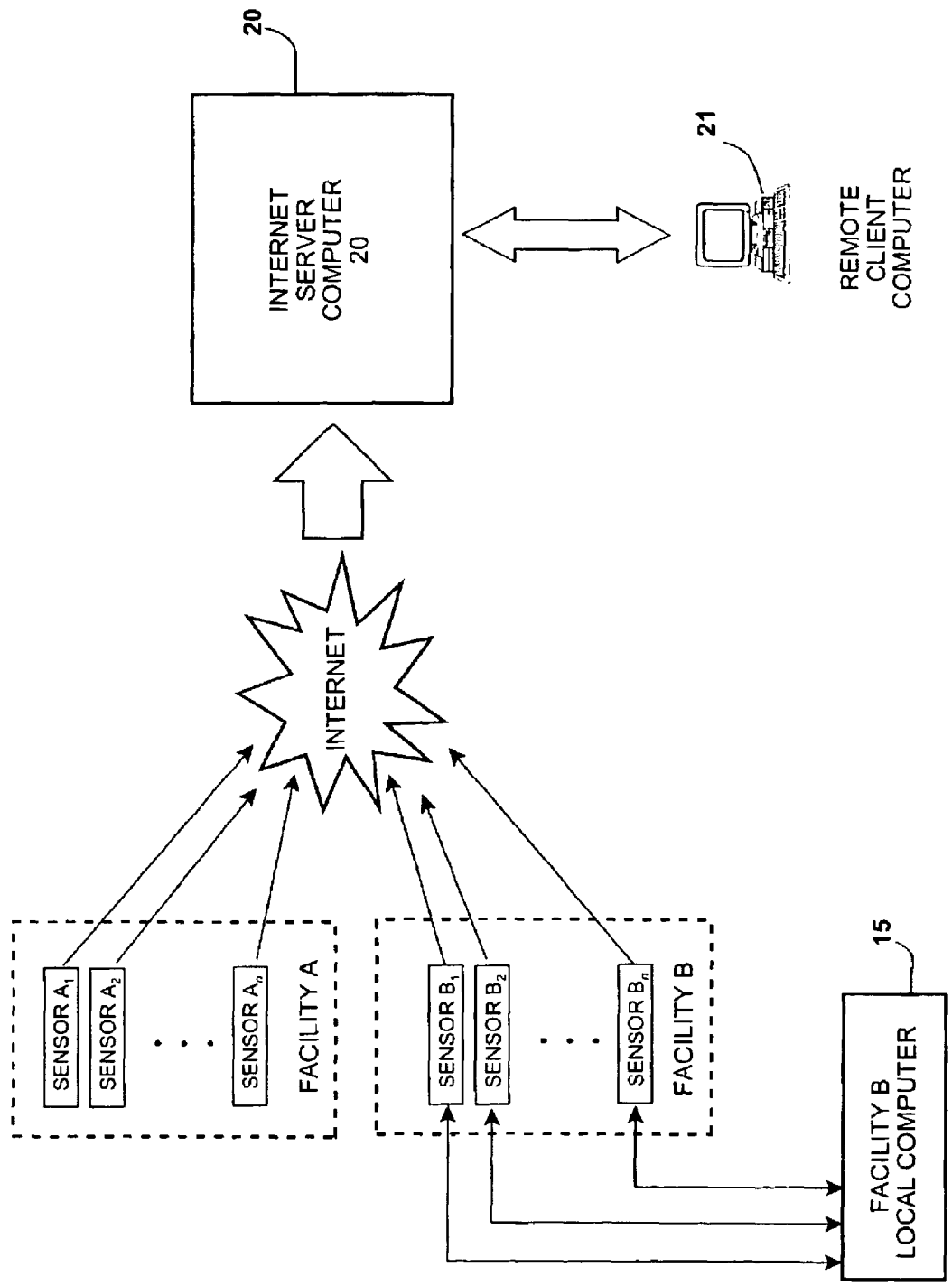
FIG. 1 illustrates an exemplary network configuration of the system of the instant invention.

FIG. 1 pictorially illustrates an exemplary arrangement in which a plurality of discrete water treatment systems, represented in the example as FACILITY A and FACILITY B, are networked to an Internet Server Computer 20 located off-site by use of local Internet access. Each facility includes at least one sensor assembly inclusive of a sensor device and a communications interface. In the illustrated example, FACILITY A includes Sensors $A_{1-n}$ which are each in communication with Internet Server Computer 20. With respect to FACILITY B, an alternative arrangement is illustrated in which the Sensors $B_{1-n}$ are networked in a parallel arrangement to both Internet Server Computer 20 and a local computer 15 located within FACILITY B.

Raw data is continuously transmitted from the sensors to the Internet Server Computer 20. Some or all the raw data relating to the critical water parameters being monitored by a sensor can be transmitted in real time. The Internet server computer 20 includes a data storage means whereby historical data may be maintained. The Internet server computer 20 has a software application running thereon which can be accessed through a Web site from a remote client computer 21 via a Web browser. In an alternative embodiment, proprietary software can be resident on the remote client computer 21 which interfaces with the Web site on Internet Server Computer 20.

Figure 2:
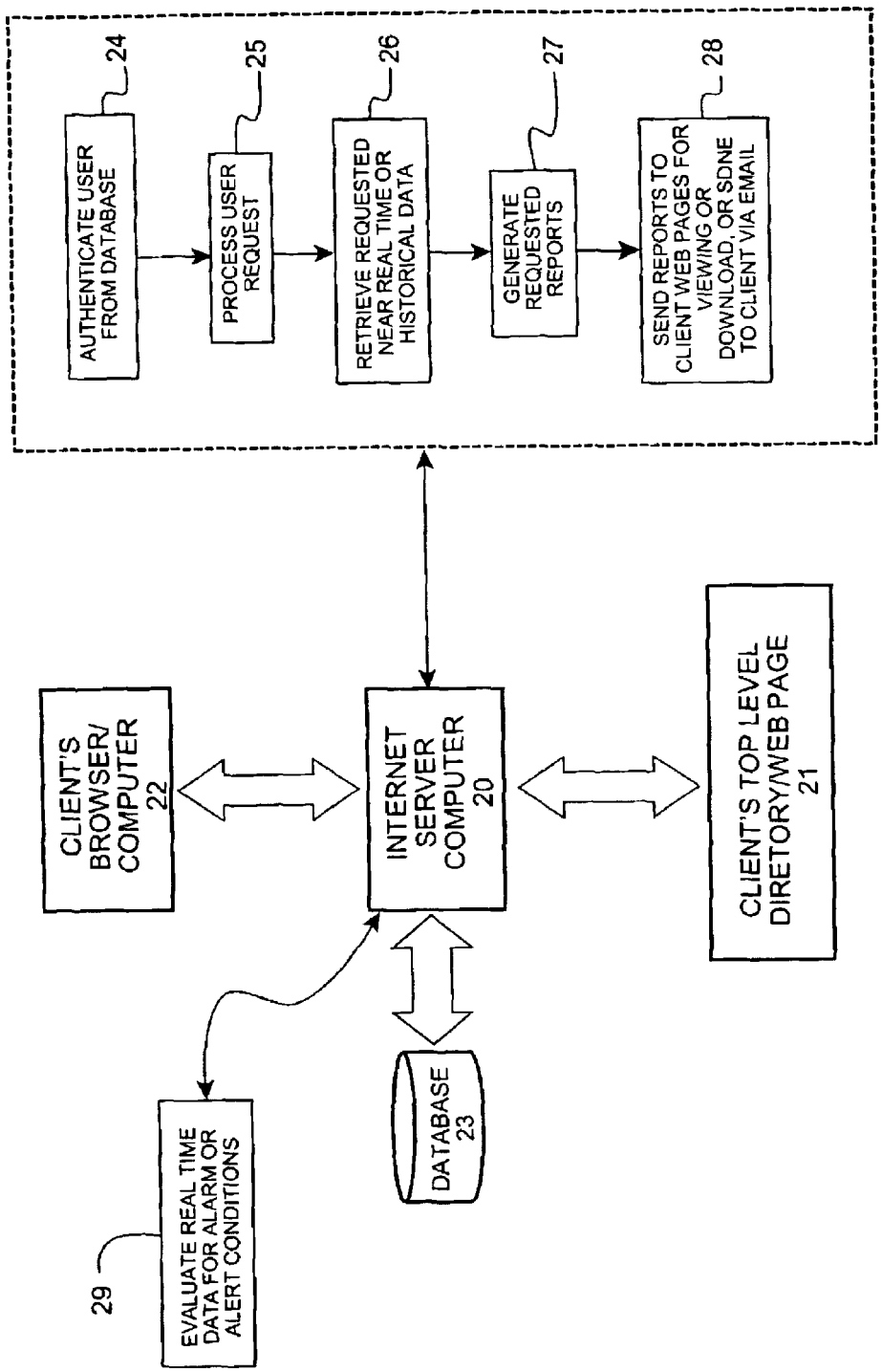
FIG. 2 is a pictorial representation of the various modules that make up the instant invention.

FIG. 2 graphically illustrates the flow of data. System operation is monitored in near real time by accessing an Internet web site 21 specifically set up for a particular customer or self configured by the customer. Data from the water or waste water treatment plant is collected on the Internet server computer 20 and stored in the database computer 23, which may be one and the same as the Internet server computer or a separate computer networked to the Internet server computer 20. As will be readily appreciated by those skilled in the art, the number and location of the Internet server computer(s) 20 and the database 23 may be varied to suit the network traffic or demands of a particular customer. The data collected on the Internet server computer 20 is also manipulated by the Internet server computer 20 wherein operating parameters are displayed graphically in a tabular format which may be color coded to provide an indication of normal operation, warning status or alarm conditions. The information from the sensors are used for determining critical information for the proper evaluation of the water treatment system which is normalized and graphically displayed for performance evaluation, preventative maintenance, scheduling, or for trouble shooting.

When the customer accesses the web site through a user request 25 the customer's credentials are compared 24 to the credentials stored in the database. If authenticated, the customer may then access near real time or historical performance data which 26 can be displayed or plotted and presented also in geographical or tabular form reports 27 for selected periods. The requested reports and displays are then placed into the client's web pages for display on the client's browser 22. This provides for not only a historical analysis of system performance, but also a record of prior performance for quality control or regulatory recording purposes.

When data arrives at the Internet server computer 20, secondary programs 29 can be executed against this data to calculate any manner of statistical inferences or derived data. These secondary programs can directly send email or text pages or voice messages or other alerts to a variety of personal communications equipment such as cell phones, pagers, Blackberrys and Palm devices. In this manner, the software is designed to continuously scan sensor input and compare the current value with alarm set points in a predetermined report. These set points may be different than actual locally set alarm points. For example, management may wish to see all instances where conditions were close to an alarm or trigger point and such conditions may be summarized in exception reports. The device further has the ability to notify authorized users by e-mail or use of a pager when process conditions meet or exceed, or appear likely to exceed, normal alarm conditions. This provides a layer of redundancy in system operation, and allows non-technical and management personnel to be notified promptly in the event of non standard operations. The local facility computer 15 shown in FIG. 1 can also include a software program operable to perform the steps of reading, querying, and storing data received from the sensor assemblies and periodically transmitting this data to the Internet server computer.

The system will automatically prepare the documentation required to meet the regulatory requirements. The documentation can be printed out and mailed or transmitted by facsimile to the regulatory agency. Ideally the regulatory report document is sent directly to the regulatory agency via electronic transmission methods such as ftp (file transfer protocol) or e-mail (smtp) thereby eliminating the opportunity for human error and/or manipulation. The device can easily be adapted to send data directly to the regulatory database in the format required by the regulatory database. The customer is capable of accessing data related to his processing equipment including all data, information and reports by use of any computer having Internet access capability. This eliminates the need for specialized equipment and allows a manager operating at his desk to access the data from any location whether it be the office, home, or on the road without the use of specialized computer systems. The software program continually updates the reports for the customer or a customer may view the reports or download them from the web site.

In the preferred embodiment, the reports are configured to particular regulatory requirements when a service agreement is established. For instance, the process system operations would contain the information necessary to monitor, maintain, supervise and trouble shoot process plant system performance. In this manner, non-limiting examples of the typical information and parameters process block would include, if applicable, flow rates, pressures, differential pressures, permeate quality, pH, alarm conditions, tank levels, and a graphical presentation of applicable process performance parameters and trends. A regulatory report would contain the information necessary to enable a regulatory agency to determine operational parameters including quality and quantity of the treated water to confirm compliance with specifications and standards. Information in this report would typically include treated water production rate (flow), treated water consumption rate (flow), treated water storage volume, reserve capacity (at current production and consumption rates), final treated water quality, reports and archive data for regulatory compliance and/or QA/QC documentation.

Calculated/estimated overall plant efficiency may be provided as a percent of theoretical efficiency. Efficiency could be based on the theoretical minimum water, power, and chemical consumption versus actual consumption calculated.

Each sensor assembly includes a communications interface which networks the sensor to the Internet server computer 20 to continuously transfer data to the computer in real time. The connection can incorporate a dedicated network connection in addition to a wireless connection. At the Internet server computer 20, the high level program also utilizes a series of configuration parameters, which may be stored in "*.ini" type files or a database to establish the path to where the raw data exists. This data is the data which needs to be analyzed, formatted and presented. The configuration file also contains the output path names to the various directories used by each client when they access their data via a web browser.

Each sensor assembly includes a communications interface which networks the sensor to the Internet server computer 20 to continuously transfer data to the computer in near real time. The connection can incorporate a dedicated network connection in addition to a wireless connection. At the Internet server computer 20, the high level executive program also utilizes a series of configuration parameters, which may be stored in "*.ini" type files or in a database to establish the paths to where the raw data exists in the sensors and where the received data is to be stored. As will be appreciated by those skilled in the art, there are many different, but effective methods, for establishing the location of the data and decoding the sent data into the appropriate rows or tables within a database. This data is the data which needs to be analyzed, formatted and presented. The configuration file also contains the output path names to the various directories used by each client when they access their data via a web browser.

Figure 3:
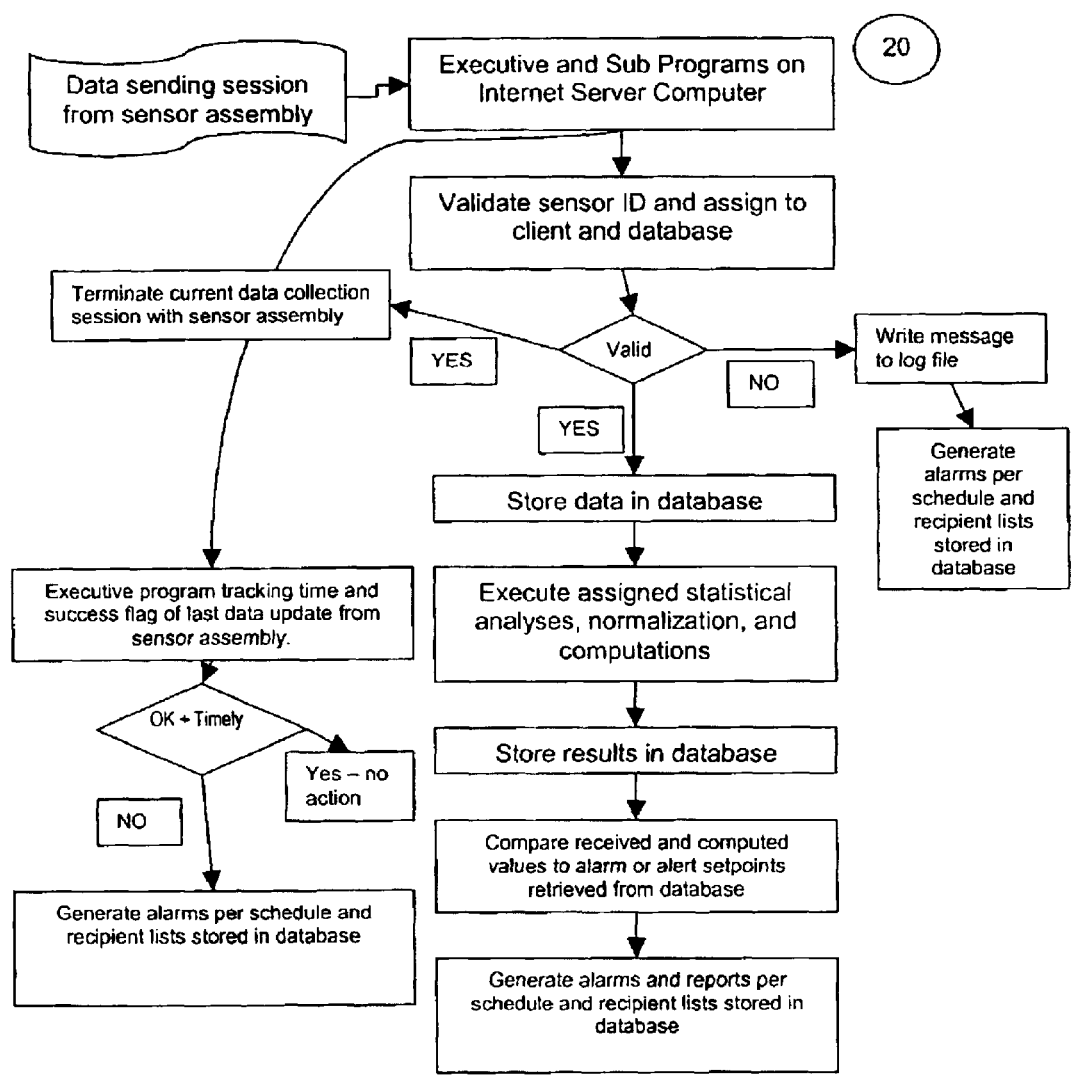
FIG. 3 is a flow diagram of the data analysis and report generator of the software.

As shown in FIG. 3, data arrives from a sensor assembly and is subsequently processed by sub-programs on the Internet server computer 20. As can be easily appreciated, the Internet server computer 20 may be in actuality a plurality of separate computers or processors designed to spread the processing load as needed. The ID of the sensor assembly is validated and if validated the data is stored in the database. Appropriate unit transformations or scaling parameters may be added from information retrieved in a configuration file or stored in the database. If the sensor ID is not validated, a message is written to a log file which may also be part of the database or a separate file. An invalid sensor ID could for example occur if a customer changed or added a sensor assembly or the customer's account was inactivated.

Any statistical or computational or normalization programs can run at this time to establish alarm conditions or derived data. For example in water treatment it is desirable to know the product of the chlorine concentration and the time it is in contact with the chlorine, known as the CT product, before entering a distribution system or in the case of secondary treatment plant the waterway. This data needs to be calculated, typically from the value provided by the chlorine sensor assembly and from the level information in the contact tank. If the CT product is too low, an alarm or alert may be generated from the calculated data.

As a further example using a reverse osmosis system as the process being monitored, the feed pressure is critical in determining the future and current performance of the system in reference to its performance when new. Furthermore, for reverse osmosis membranes, changes in pressure are related to age, production rate, and temperature. Thus a change in flow rate may or may not indicate that the overall system's performance has changed when normalized and compared to its performance when new or recently cleaned. Prior to this invention, the complex mathematics for these conversions required some manual intervention on the part of the operator to compute the normalized conditions. The instant invention does this automatically and reports normalized data to the output.

Of course, many more process parameters are monitored, normalized, and analyzed by the computer software of this invention. The results of these analyses are then utilized in the following manner:

Raw performance data compared to normalized or corrected data is plotted in simple, easy to understand graphs which are published as html or in pdf, jpeg, gif, or other format readily usable by a web browser. The performance is compared to predicted normalized performance and if the differential exceeds preset limits (found in the configuration information) selected individuals are automatically sent E-mail or in more extreme cases a pager or fax (paper) alert. Process and regulatory reports are prepared from the data and published in a variety of formats for access by a web browser, including Excel spreadsheets, pdf files, text documents, and html tables. Historical data is regularly updated by the data coming into the system and new graphs and reports are either produced on demand from the user via a browser request or prepared and stored on the web pages as noted. Scheduled maintenance requirements are reviewed by the software and if needed within a preset time—usually within one week, or E-mail notification is sent to the designated individual(s).

In either case, the output is sent to the designated web directories on a web server attached to the Internet. These directories are appropriately protected for access only by authorized individuals. It may be appreciated that the physical location of the Main Data Computer, the ftp server, and the web server may be at the same location or remote from each other. In addition mirror sites can be maintained as necessary to provide reliable service. The main computer may be either a stand alone unit or can serve as the Internet web server in itself in addition to performing the actual computations. No particular operating system is preferred for the web server and either Microsoft Windows or UNIX may be utilized depending on convenience, reliability, and cost issues.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A method for remotely monitoring the operating performance parameters for a water treatment system, comprising the steps of:

a) providing at least one sensor assembly effective for monitoring critical water parameters and transmitting raw operating data via a communications interface;
   b) coupling at least one said sensor to an Internet server computer via said communications interface;
   c) transmitting said raw data using to a remotely located Internet server computer;
   d) storing said transmitted raw data on said Internet server computer;
   e) accessing such data asynchronously from said Internet server computer;
   f) manipulating said transmitted and stored raw data into an analysis result and a report result; and
   g) uploading said analysis result and said report result to an Internet web server in a format suitable for access and visualization with a web browser computer program.

2. The method of claim 1, further including a step of filing said report result with an appropriate regulatory agency.

3. The method of claim 1, further including a step of transmitting said report result directly to an appropriate regulatory agency using electronic transmission means.

4. The method of claim 3, wherein said electronic transmission means is via e-mail.

5. The method of claim 3, wherein said electronic transmission means is via ftp (file transfer protocol).

6. The method of claim 3, wherein said electronic transmission means is via direct connection over the Internet to a database located on a remote computer.

7. The method of claim 1, wherein said step of manipulating said transmitted and stored raw data includes routines to notify selected individuals on the basis of the stored parameters relating to the performance of the system being analyzed.

8. The method of claim 1, wherein said step of manipulating said raw data includes routines to notify selected individuals on the basis of said selected parameters relating to compliance testing dates and performance criteria.

9. The method of claim 1, wherein said step of accessing said raw operating data from said at least one sensor includes the steps of reading, querying, and storing data accessed from said electronic system by use of said communications card interface.

10. The method of claim 1, wherein said communications interface is integral to said sensor assembly.

11. The method of claim 1, wherein said at least one sensor assembly is operable to transmit raw operating data in real time.

12. The method of claim 1, wherein said water treatment system produces potable water.

13. The method of claim 1, wherein said water treatment system includes secondary and/or tertiary treatment.

14. The method of claim 1, wherein said sensor assemblies communicate with an electronic control system.

15. The method of claim 14, wherein said step of transmitting said raw data to said Internet Server Computer is integrated into said electronic control system.

16. The method of claim 14, wherein said electronic control system is defined as a programmable logic controller (PLC).

17. The method of claim 1, wherein at least one sensor assembly is in communication with a local computer and said Internet computer in a parallel arrangement effective for simultaneous transmission of said raw operating data, and said local computer includes a software program operable to perform the steps of reading, querying, and storing data accessed from said at least one sensor.

18. The method of claim 1, further including the steps of:
h) comparing said analysis result with known optimum performance parameters;
i) determining differentials between said known optimum performance parameters and the analysis result; and
j) sending notifications to pre-determined recipients if known limits for said differentials are exceeded.

19. The method of claim 1, further including the steps of:
h) comparing said analysis result with known Federal and State EPA parameters;
i) determining differentials between said known Federal and State EPA parameters and the analysis result; and
j) sending notifications to pre-determined recipients if known limits for differentials are exceeded.

20. The method of claim 1, further including the steps of:
h) comparing said report result with know Federal and State EPA parameters;
i) determining the differential between said known Federal and State parameters and the report result; and
j) sending notifications to pre-determined recipients if known limits for said differentials are exceeded.

21. The method of claim 1, further including the steps of converting said transmitted and stored raw operating data into visual graphs.

22. The method of claim 1, further including the steps of converting said transmitted and stored raw operating data into statistical reports.

23. The method of claim 1, further including the steps of converting said transmitted and stored raw operating data into a compliance calendar.

* * * * *